(12) United States Patent
Sasaki et al.

(10) Patent No.: US 8,304,573 B2
(45) Date of Patent: Nov. 6, 2012

(54) RECOVERY METHOD OF PYROLYSIS PRODUCT OF RESIN

(75) Inventors: Akinobu Sasaki, Otake (JP); Nobuyuki Kikuya, Otake (JP); Takashi Ookubo, Otake (JP); Masahiro Hayashida, Otake (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 511 days.

(21) Appl. No.: 12/529,725

(22) PCT Filed: Mar. 7, 2008

(86) PCT No.: PCT/JP2008/054153
§ 371 (c)(1),
(2), (4) Date: Sep. 3, 2009

(87) PCT Pub. No.: WO2008/108461
PCT Pub. Date: Sep. 12, 2008

(65) Prior Publication Data
US 2010/0121097 A1 May 13, 2010

(30) Foreign Application Priority Data

Mar. 7, 2007 (JP) ................................ 2007-057742
Mar. 7, 2007 (JP) ................................ 2007-057773

(51) Int. Cl.
*C07C 67/333* (2006.01)
*C07C 67/52* (2006.01)
*C07C 69/54* (2006.01)

(52) U.S. Cl. ...................................... 560/205; 560/218
(58) Field of Classification Search ........................ None
See application file for complete search history.

(56) References Cited

U.S. PATENT DOCUMENTS

| 3,974,206 A | | 8/1976 | Tatsumi et al. |
| 4,423,688 A | * | 1/1984 | Kuo ............................. 110/245 |
| 6,469,203 B1 | | 10/2002 | Weiss et al. |

FOREIGN PATENT DOCUMENTS

| EP | 0 600 727 A2 | 6/1994 |
| EP | 0 600 727 A3 | 6/1994 |
| JP | 51 42374 | 4/1976 |
| JP | 54 83002 | 7/1979 |
| JP | 59 111815 | 6/1984 |
| JP | 6 228569 | 8/1994 |
| JP | 7 89900 | 4/1995 |
| JP | 9 235563 | 9/1997 |
| JP | 2001-323283 | 11/2001 |
| JP | 2002 526466 | 8/2002 |
| WO | WO 2005/084839 A1 | 9/2005 |

OTHER PUBLICATIONS

Extended European Search Report issued on Nov. 29, 2010, in Application No. 08721571.1.
W. Kaminsky, et al., "Monomer recovery by pyrolysis of poly(methyl methacrylate) (PMMA)", Journal of Analytical and Applied Pyrolysis, Elsevier Science Publishers B.V., vol. 19, XP026508097, Jul. 1, 1991, pp. 311-318.

* cited by examiner

*Primary Examiner* — Yevegeny Valenrod
(74) *Attorney, Agent, or Firm* — Oblon, Spivak, McClelland, Maier & Neustadt, L.L.P.

(57) ABSTRACT

A method of recovering pyrolysis products of resin of the present invention includes cooling gaseous pyrolysis products generated from pyrolysis of the resin in a pyrolysis tank to recover the resin as liquid pyrolysis products. The method includes the following steps (1) to (4): (1) continuously feeding fluidization gas, heated solid particles, and a resin into the pyrolysis tank to fluidize the solid particles and the resin by the fluidization gas; (2) continuously feeding the resin into the pyrolysis tank from a position which is ½ or less of the height of a solid particle layer in the pyrolysis tank in a stationary state; (3) continuously discharging the solid particles from a position lower than the height of a feeding position of the resin; and (4) heating the discharged solid particles in a heating furnace and then feeding the heated solid particles into the pyrolysis tank.

20 Claims, 5 Drawing Sheets

US 8,304,573 B2

RECOVERY METHOD OF PYROLYSIS PRODUCT OF RESIN

TECHNICAL FIELD

The present invention relates to a method of recovering pyrolysis products resulting from pyrolysis of a resin. More particularly, the present invention relates to a method of recovering pyrolysis products while continuously supplying a pyrolysis tank with resin, solid particles, and fluidization gas.

Priority is claimed on Japanese Patent Application No. 2007-057742, filed Mar. 7, 2007, and Japanese Patent Application No. 2007-057773, filed Mar. 7, 2007, the contents of which are incorporated herein by reference.

BACKGROUND ART

As a method of pyrolyzing a resin, a method of supplying a pyrolysis tank with a resin and high-temperature solid particles and pyrolyzing the resin while fluidizing them with fluidization gas is known. Another method of pyrolyzing a resin in the atmosphere of inert gas such as nitrogen is also known. In these methods, the amount of heat required for pyrolyzing the resin is supplied by the high-temperature solid particles. Accordingly, the methods are advantageous industrially.

As the above-mentioned method of pyrolyzing the resin, the following methods are known.

Patent Document 1 discloses a method of feeding solid waste to a high-temperature fluidized bed, in which solid waste is cooled to prevent thermally-melted materials from being attached thereto by allowing cooling gas between a screw shaft and a screw outer pipe in resin feeding equipment so as to come in direct contact with the solid waste and a rotational force is applied to a fluid medium to destruct bridges of the solid waste and to accomplish a smooth flow by allowing the cooling gas to flow in a fluidized bed in a tangential direction thereof.

However, the method disclosed in Patent Document 1 has a problem with an increase in cost for allowing the cooling gas to flow and a decrease in temperature of the fluidized bed due to the flow of the cooling gas.

Patent Document 2 discloses a method of recovering pyrolysis products, by mixing waste plastic with high-temperature sand by means of mechanical agitation and directly heating the waste plastic to pyrolyze the waste plastic.

In this method, since a pyrolysis tank for pyrolyzing the waste plastic is fluidized by the use of an agitator, there is a problem that the fluidization is not sufficient only by the use of the agitator and long-term stable operation is difficult. Depending on the temperature or the waste plastic condition, there is a problem that the flow in the pyrolysis tank is completely stopped. This method also has a problem in that the pyrolysis products are not smoothly discharged from the pyrolysis tank system and the recovered pyrolysis products decrease in quality. In case of large-sized equipment, a lot of agitating torque is necessary for maintaining the mixture state in the pyrolysis tank well, thereby increasing the equipment cost and the operation cost.

Regarding positions for supplying the waste plastic in the method, the waste plastic is fed from the upper portion of the equipment when the pyrolysis equipment is of a vertical type (see FIG. 3 of Patent Document 2). When the pyrolysis equipment is of a horizontal type (see FIG. 5 of Patent Document 2), the waste plastic is fed from the upper portion of the most upstream device of the equipment.

The waste plastic is pyrolyzed while allowing the waste plastic and high-temperature sand to move from the upper portion to the lower portion or from the upstream to the downstream depending on the feeding positions. However, when fluidization gas is supplied in the method, the mixture of the waste plastic and the high-temperature sand is deteriorated, thereby not efficiently recovering the pyrolysis products from the waste plastic.

Patent Document 3 discloses a method of recovering gas or oil from waste plastic by means of pyrolysis by mixing the waste plastic with thermal storage mediums.

This method includes a step of forming a movable bed formed of thermal storage mediums in a reactor, a step of introducing waste plastic into the reactor and pyrolyzing the waste plastic by means of heat of the thermal storage mediums while moving the waste plastic along with the movable bed, a step of extracting and recovering volatile pyrolysis products of the waste plastic from the upper portion of the reactor, a step of introducing high-temperature steam into a lower layer of the movable bed in the reactor to serve as carrier gas for discharging the pyrolysis products of the waste plastic out of the system and re-pyrolyzing the waste plastic by means of thermal energy of the high-temperature steam, and a step of discharging the pyrolysis products, non-volatile unpyrolyzed materials, and the thermal storage mediums from the lower portion of the reactor.

However, in the system in which the thermal mediums are stacked in the pyrolysis tank, the flow in the pyrolysis tank is not sufficient and the temperature distribution or the waste plastic distribution in the pyrolysis tank is not uniform. Accordingly, the volume of the equipment cannot be efficiently used.

Since the fed waste plastic can be easily lumped, pyrolysis heat is not efficiently transmitted to the waste plastic, thereby reducing the throughput. When the lump of the waste plastic becomes greater, it clogs the inside of the equipment, thereby making stable operation difficult.

Patent Document 4 discloses a method of pyrolyzing solid waste by allowing a mixture layer of solid waste and solid thermal medium to flow by the use of an agitator in a pyrolytic furnace. However, in this method, since the mixture of the solid waste and the thermal medium is made to flow only by the use of the agitator, there is a problem that the flow is not sufficient and a long-term stable operation is not possible.

Patent Document 5 discloses a method of pyrolyzing thermoplastics by bringing the thermoplastics into contact with a fluidized bed of heated solid particles. In this method, since steam is used as fluidization gas in a pyrolysis step, there is a problem that the flow is not sufficient only by the use of the steam and a long-term stable operation is not possible. For example, when it is intended to pyrolyze methacryl resin including methyl methacrylate units, since the boiling points of methyl methacrylate and water are substantially equal to each other (100° C.), it is not substantially possible that only methyl methacrylate is in a liquid state and steam is in a gaseous state. In order to circulate steam for use, both methyl methacrylate and steam should be made to be liquids, methyl methacrylate should be separated from water, and then the water should be heated to generate steam, thereby complicating the processes. There is also a problem that the method cannot be used for resin having a boiling point higher than that of water.

Patent Document 6 discloses a method of pyrolyzing methacryl resin by bringing the methacryl resin into contact with a high-temperature thermal medium fluidized mechanically. In this method, since the inside of a pyrolysis tank is fluidized only by the use of an agitator without using any gas, there is a problem that the flow in the pyrolysis tank is not sufficient and a long-term stable operation is not possible. There is also a problem that the flow in the pyrolysis tank is completely stopped depending on the temperature condition or the resin condition. This method has a problem that the pyrolysis products of the resin cannot be smoothly discharged from the pyrolysis tank system and the recovered pyrolysis products decrease in quality.

Patent Document 1: Japanese Laid-Open Patent Application No. 51-42374
Patent Document 2: Japanese Laid-Open Patent Application No. 9-235563
Patent Document 3: Japanese Laid-Open Patent Application No. 6-228569
Patent Document 4: Japanese Laid-Open Patent Application No. 54-83002
Patent Document 5: Japanese Laid-Open Patent Application No. 59-111815
Patent Document 6: Published Japanese Translation No. 2002-526466 of PCT

SUMMARY OF THE INVENTION

Problems to be Solved by the Invention

An object of the present invention is to provide a method allowing a long-term continuous operation in an industrial scale in feeding fluidization gas from the lower portion of a pyrolysis tank and continuously feeding heated solid particles for giving the amount of heat necessary for pyrolyzing resin. Particularly, an appropriate resin feeding position and an appropriate solid particle discharging position in a pyrolysis tank are provided.

Means for Solving the Problems

The first aspect of the present invention is a method of recovering pyrolysis products of a resin as liquid pyrolysis products by cooling gaseous pyrolysis products generated from pyrolysis of the resin in a pyrolysis tank, the method comprising the following steps (1) to (4):

(1) continuously feeding fluidization gas, heated solid particles, and a resin into the pyrolysis tank to fluidize the solid particles and the resin by the fluidization gas;

(2) continuously feeding the resin into the pyrolysis tank from a position which is ½ or less of the height of a solid particle layer in the pyrolysis tank in a stationary state;

(3) continuously discharging the solid particles from a position lower than the height of a feeding position of the resin; and (4) heating the discharged solid particles in a heating furnace and then feeding the heated solid particles into the pyrolysis tank.

The second aspect of the present invention is a method of recovering pyrolysis products of a resin as liquid pyrolysis products by cooling gaseous pyrolysis products generated from pyrolysis of the resin in a pyrolysis tank, the method comprising the following steps (1) to (7):

(1) continuously feeding heated solid particles, fluidization gas, and a resin into the pyrolysis tank, provided that the fluidization gas is fed from the lower portion of the pyrolysis tank;

(2) setting the temperature T of the pyrolysis tank to the range of 350° C. to 500° C.;

(3) fluidizing the solid particles and the resin with an agitator disposed in the pyrolysis tank and the fluidization gas;

(4) setting a ratio A/B of a feeding rate of the fluidization gas A (kg/hr) to a feeding rate of the solid particles B (kg/hr) to the range of 0.04 to 0.3;

(5) continuously discharging the solid particles from the pyrolysis tank while the mean residence time of the solid particles in the pyrolysis tank is maintained to the range of 0.5 to 1.5 hr;

(6) discharging mixture gas of the gaseous pyrolysis products generated from the resin pyrolyzed by sensible heat of the solid particles and the fluidization gas from the pyrolysis tank and cooling the mixture gas in a cooling unit to liquefy the pyrolysis products; and (7) separating the fluidization gas from the cooled mixture gas and feeding the separated fluidization gas into the pyrolysis tank again.

According to the present invention, it is possible to continuously pyrolyze the resin stably in an industrial scale for a long period of time, thereby efficiently obtaining pyrolysis products of the resin.

BRIEF DESCRIPTION OF THE REFERENCE SYMBOLS

Figure 1:
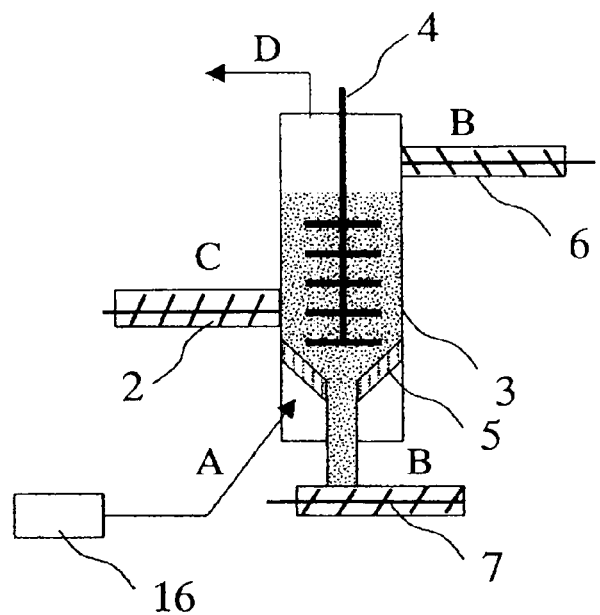
FIG. 1 is a diagram illustrating the first embodiment of a pyrolysis tank used in the present invention.

A: Fluidization gas
B: Solid particle (sand)
C: Resin
D: Mixture of fluidization gas and pyrolysis product
1: Resin hopper
2: Resin feeding unit
3: Pyrolysis tank
4: Agitator
5: Distributing plate
6: Solid particle feeding unit
7: Solid particle discharging unit
8: Heating furnace
9: Cooling unit
10: Recovering container
11: Mist recovering unit
12: Recovering container
13: Circulating blower
14: Gas feeding blower
15: Flow rate controlling unit
16: Controlling unit of temperature of fluidization gas
17, 20: Height of solid particle layer
18, 21: Length of space portion
19, 22: Total height of pyrolysis tank

BEST MODE FOR CARRYING OUT THE INVENTION

The first embodiment of the present invention will be described below.

Figure 6:
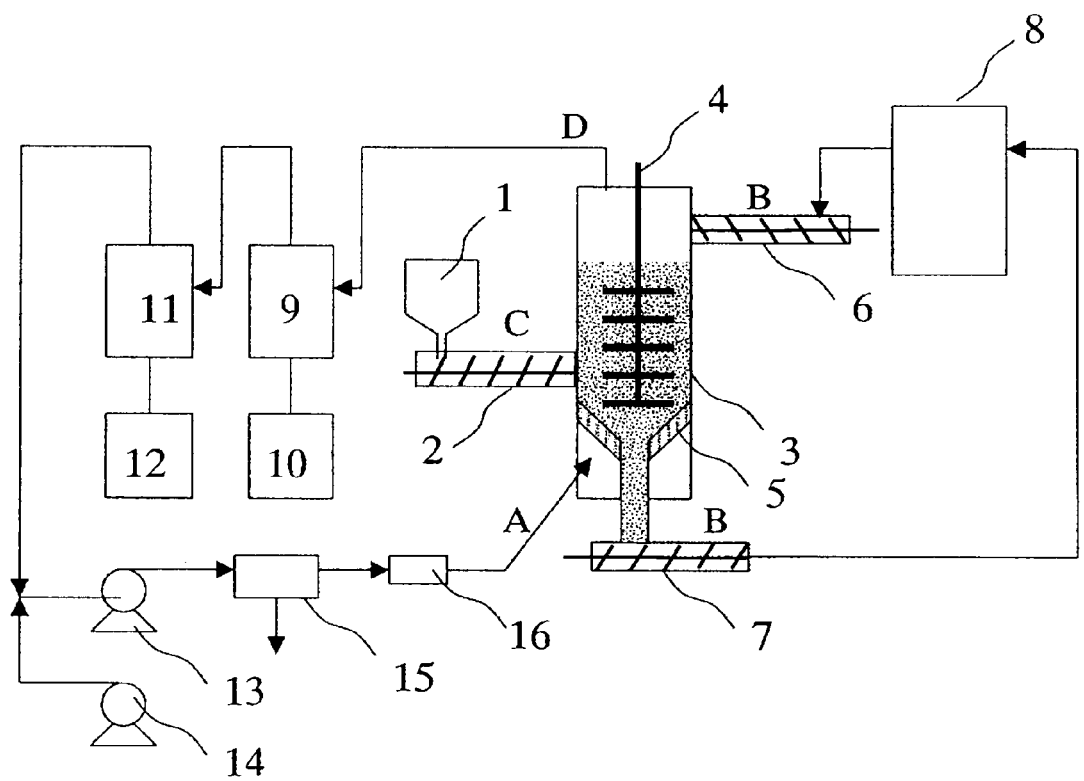
FIG. 6 is a general diagram illustrating equipment for putting the invention into practice.

For example, as shown in FIG. 6, equipment for putting the first embodiment into practice includes a pyrolysis tank 3 for pyrolyzing resin C, a heating furnace 8 for heating solid particles B, and a cooling unit 9 for recovering pyrolysis products.

The solid particles B heated in the heating furnace 8 are continuously fed to the pyrolysis tank 3. Fluidization gas A for mixing and fluidizing the solid particles B and the resin C is continuously fed from the lower portion of the pyrolysis tank 3.

The temperature of the pyrolysis tank 3 is determined depending on heat balances such as the feeding rate of the resin C, the feeding temperature thereof, the amount of heat necessary for pyrolyzing the resin C, the feeding rate of the solid particles B, the feeding temperature thereof, the feeding rate of the fluidization gas A, the feeding temperature thereof, and the amount of heat discharge from the pyrolysis tank. The temperature of the pyrolysis tank 3 is preferably in the range of 350° C. to 500° C. When the temperature of the pyrolysis tank 3 is 350° C. or more, a pyrolysis rate of the resin C can be increased. When the temperature of the pyrolysis tank is 500° C. or less, the quality of a liquid recovered by pyrolysis of the resin C is improved.

The resin C is continuously fed to the pyrolysis tank 3. A feeding port of the resin C is disposed at a position which is ½ or less of the height of a solid particle layer in the pyrolysis tank 3 in a stationary state on the outer surface of the pyrolysis tank 3.

The "stationary state" means a state where the feeding of the fluidization gas A and the resin C into the pyrolysis tank 3 are stopped and the discharging and the feeding of the solid particles B are stopped in a state where the resin C is not fed. When an agitator 4 is used, the "stationary state" means a state where the agitator 4 is additionally stopped in the above-mentioned state.

The "solid particle layer" means a layer formed of the solid particles.

Figure 7:
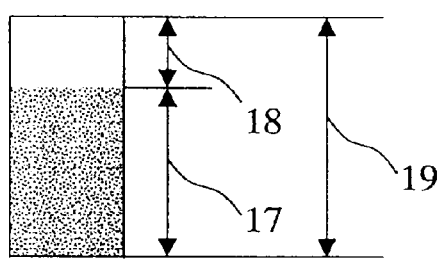
FIG. 7 is a diagram illustrating the first embodiment of the height of a solid particle layer, the length of a space portion, and the total height of a pyrolysis tank.
Figure 8:
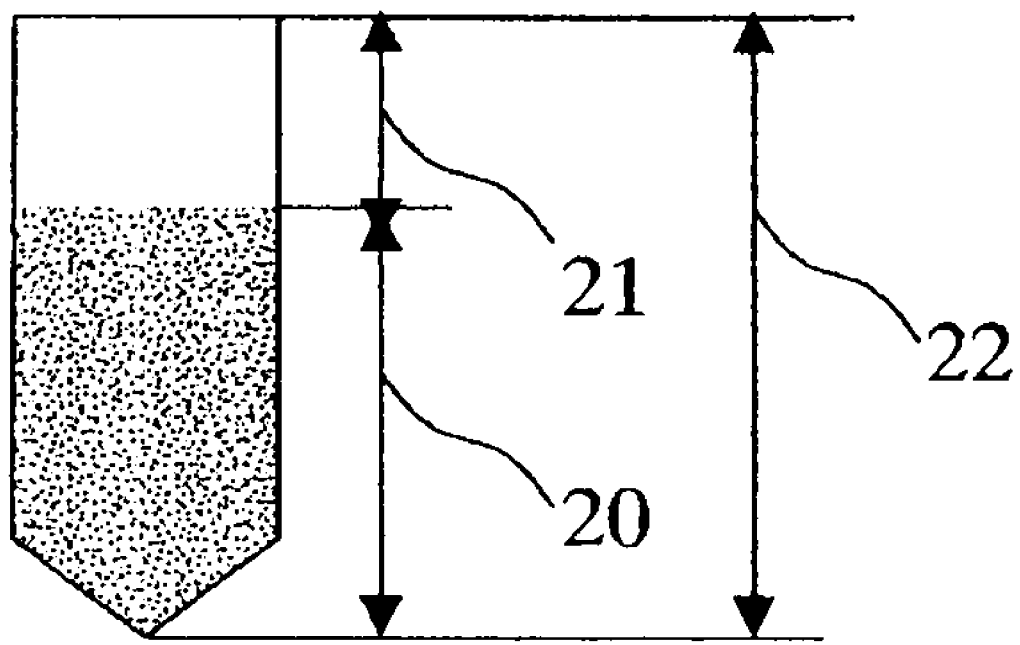
FIG. 8 is a diagram illustrating the second embodiment of the height of a solid particle layer, the length of a space portion, and the total height of a pyrolysis tank.

The "height of the solid particle layer" means a distance 17 from the lowermost surface of the pyrolysis tank 3 to the uppermost surface of the solid particle layer (FIG. 7), when the lowermost surface of the pyrolysis tank 3 has a flat shape. When the lowermost surface of the pyrolysis tank 3 has a cone shape, the "height of the solid particle layer" means a distance 20 from a vertex-corresponding position of the cone shape (hereinafter, also referred to as "vertex of a cone") to the uppermost surface of the solid particle layer (FIG. 8).

The height 17 or 20 of the solid particle layer in a stationary state is not particularly limited, but is preferably set so that a ratio of the height 17 or 20 of the solid particle layer in a stationary state to the representative length of the pyrolysis tank 3 is in the range of 0.5 to 3.5. The representative length of the pyrolysis tank 3 is a diameter of a circle when the sectional shape of the pyrolysis tank 3 is the circle, is a length of one side when the horizontal sectional shape of the pyrolysis tank 3 is a square, and is a half of the sum of a short side and a long side, when the horizontal sectional shape of the pyrolysis tank 3 is a rectangle. When the horizontal section has other shapes, a sectional area is first calculated and then the representative length is the diameter of a circle having the same sectional area as the calculated sectional area.

By setting the ratio of the representative length of the pyrolysis tank 3 to the height 17 or 20 of the solid particle layer in a stationary state to be 0.5 or more, a non-uniform flow of the solid particles B decreases. By setting the ratio of the representative length of the pyrolysis tank 3 to the height 17 or 20 of the solid particle layer in a stationary state to be 3.5 or less, the pressure drop of the solid particle layer is reduced, thereby reducing the power necessary for feeding the fluidization gas A.

The "representative length of the pyrolysis tank" means a representative length of a horizontal section of the pyrolysis tank.

A space portion is preferably disposed above the solid particle layer. Here, the "space portion" means a space from the uppermost surface of the solid particle layer to the uppermost surface of the pyrolysis tank 3. A length 18 or 21 of the space portion in a stationary state is preferably set so that a ratio of the length 18 or 21 of the space portion in a stationary state to the representative length of the pyrolysis tank 3 is in the range of 0.5 to 5.0. The representative length of the pyrolysis tank 3 is the diameter of a circle when the sectional shape of the pyrolysis tank 3 is the circle, is a length of one side when the horizontal sectional shape of the pyrolysis tank 3 is a square, and is a half of the sum of a short side and a long side when the horizontal sectional shape of the pyrolysis tank 3 is a rectangle. When the horizontal section has other shapes, a sectional area is first calculated and then the representative length is a diameter of a circle having the same sectional area as the calculated sectional area.

By setting the ratio of the representative length of the pyrolysis tank 3 to the length 18 or 21 of the space portion in a stationary state to be 0.5 or more, it is possible to reduce the amount of the solid particles B included in a mixture of the fluidization gas A and the pyrolysis products of the resin C sent from the pyrolysis tank 3 to the cooling unit 9. By setting the ratio of the representative length of the pyrolysis tank 3 to the length 18 or 21 of the space portion in a stationary state to be 5 or less, the total height of the pyrolysis tank 3 can be made to be low, thereby reducing the equipment cost of the pyrolysis tank 3.

The total height of the pyrolysis tank 3 is preferably set so that a ratio of the representative length of the pyrolysis tank 3 to the total height 19 or 22 of the pyrolysis tank is in the range of 1 to 8.5. The total height 19 or 22 of the pyrolysis tank 3 is a distance from the vertex of a cone to the uppermost surface of the pyrolysis tank 3 when the lowermost surface of the pyrolysis tank 3 has a cone shape and is a distance from the lowermost surface of the pyrolysis tank 3 to the uppermost surface of the pyrolysis tank 3 when the lowermost surface of the pyrolysis tank 3 has a plane shape. By setting the ratio of the representative length of the pyrolysis tank 3 to the total height 19 or 22 of the pyrolysis tank to be 1 or more, it is possible to reduce the non-uniform flow of the solid particles B and to secure the space portion. By setting the ratio of the representative length of the pyrolysis tank 3 to the total height 19 or 22 of the pyrolysis tank to be 8.5 or less, it is possible to reduce the pressure drop of the solid particle layer. In addition, since the total height 19 or 22 of the pyrolysis tank decreases, it is possible to reduce the equipment cost for the pyrolysis tank 3.

When the fluidization gas A is fed into the pyrolysis tank 3, the resin C moves up in the pyrolysis tank 3 because the specific density of the resin C is smaller than that of the solid particles B. By feeding the resin C from a position which is provided on the outer surface of the pyrolysis tank 3 and is ½ or less of the height of the solid particle layer in the pyrolysis tank 3 in a stationary state, the resin C is dispersed into the solid particles B while moving up in the pyrolysis tank 3. As a result, the resin C is satisfactorily dispersed in the solid particles B, therefore, the resin C is stably pyrolyzed in the pyrolysis tank 3. If the resin C is fed into the pyrolysis tank 3 from a position higher than a half of the height 17 or 20 of the solid particle layer in a stationary state, the resin C exists only in the upper portion of the pyrolysis tank 3. As a result, since the fluidity in the upper portion is deteriorated, the temperature decreases and thus the unpyrolyzed resin C stays in the pyrolysis tank 3 for a long time.

It is preferable that the resin is fed in a pellet shape (solid particle shape). By feeding the resin in the pellet shape, the dispersion of the resin in the pyrolysis tank is improved. The particle size of the resin pellets is not particularly limited, however, it is preferable that the resin pellets have an average particle size of 1 to 20 mm from the point of view of treatment, feeding stability, and dispersibility in the pyrolysis tank. By setting the average particle size to be 1 mm or more, it is possible to prevent attachment or fusion bonding between the resin pellets. By setting the average particle size to be 20 mm or less, the dispersibility of the resin pellets into the solid particles is improved. Particularly, the average particle size of the resin pellets is preferably in the range of 3 to 10 mm.

The temperature of the resin fed into the pyrolysis tank is not particularly limited as long as the resin has a pellet shape, but it is preferable that the temperature of the resin is in the range of 0° C. to (Tg−50)° C. or the range of 0° C. to (Tm−50)° C. Here, Tg represents the glass transition temperature of the resin and Tm represents the melting point of the resin. From the point of view of prevention of a decrease in temperature of the pyrolysis tank or retention of fluidity in the pyrolysis tank, it is preferable that the temperature of the resin is 0° C. or more. From the point of view of preventing the fusion bonding between the resin pellets to improve the dispersibility of the resin pellets in the solid particles, it is preferable that the temperature of the resin is (Tg−50)° C. or less, or (Tm−50)° C. or less.

In the first embodiment, the solid particles in the pyrolysis tank are continuously discharged from a position lower than the height of the feeding position of the resin. The resin is hardly mixed into the solid particles discharged from the position lower than the height of the feeding position of the resin. Accordingly, it is possible to secure the fluidity of the solid particles, thereby increasing the amount of pyrolysis products to be recovered. If the solid particles are discharged from a position as high as the feeding position of the resin or higher than it, a great amount of resin is mixed into the solid particles. Accordingly, the fluidity and the discharging property of the solid particles are deteriorated, thereby reducing the amount of the pyrolysis products to be recovered.

The feeding position of the solid particles to be fed continuously into the pyrolysis tank is not particularly limited. Since the inside of the pyrolysis tank is fluidized by the fluidization gas, the solid particles can be easily fluidized uniformly in the pyrolysis tank even when they are fed from any position.

It is preferable to provide the pyrolysis tank with an agitator, because the flow of the resin and the solid particles is further improved. The agitator includes a rotating body for agitation, a shaft, and an agitating blade. The shape of the agitating blade is not particularly limited and examples thereof include a paddle blade, an anchor blade, a ribbon blade, a helical blade, a propeller blade, and a turbine blade.

The inside of the pyrolysis tank is held at a high temperature and the resin fed into the pyrolysis tank is pyrolyzed. Gaseous pyrolysis products are generated by pyrolyzing the resin and the gaseous pyrolysis products are guided to the cooling unit by the fluidization gas. Unpyrolyzed materials are introduced into a heating furnace along with the solid particles. The gaseous pyrolysis products mean pyrolysis products which are in a gaseous state at the temperature of the pyrolysis tank. By sending the gaseous pyrolysis products to the cooling unit and cooling the gaseous pyrolysis products, they can be recovered as a liquid. Some of the gaseous pyrolysis products may not be changed to the liquid state by the cooling and thus may not be recovered. An example thereof is carbon dioxide.

The "unpyrolyzed materials" are the resin itself; resin having decreased in molecular weight, or carbonized materials. The unpyrolyzed materials are in the pyrolysis tank in a state where they are attached to the surfaces of the solid particles or in a state where they are mixed with the solid particles. The mixture of the solid particles and the unpyrolyzed resin is introduced to and heated by the heating furnace, and only the unpyrolyzed materials are removed by pyrolysis or combustion. Since the temperature of the solid particles increases in the heating furnace, the solid particles are fed to the pyrolysis tank again for use.

The fuel used in the heating furnace is not particularly limited and examples thereof include heavy oil, light oil, lamp oil, and the liquid recovered by pyrolyzing the resin. Particularly, when the recovered liquid is used, it is not necessary to purchase a fuel; therefore, it is advantageous from the point of view of environment and cost. Since the amount of heat necessary for pyrolyzing the resin are supplied from the recovered liquid, the use of the recovered liquid provides a closed system, thereby providing a process having a small environmental load.

The solid particles are not particularly limited and examples thereof include sand, ceramic particles, metal particles, metal oxide particles, metal hydroxide particles, and metal halide particles. The solid particles may be used alone or in combination of two or more kinds. The solid particles may be inert to the pyrolysis of the resin, may be a catalyst promoting the pyrolysis of the resin, or may absorb harmful materials generated from the resin. For example, when resin including chlorine atoms in molecules, such as polyvinyl chloride resin, is heated and pyrolyzed, toxic materials such as chlorine, hydrogen chloride, and chlorine-containing materials are generated. It is preferable that the solid particles such as calcium oxide, calcium hydroxide, and calcium carbide neutralizes or absorbs chlorine, hydrogen chloride, and chlorine-containing materials.

The size of the solid particles is not particularly limited, but the average particle size is preferably in the range of 0.01 mm to 1 mm and more preferably in the range of 0.05 mm to 0.8 mm from the point of view of handling property, miscibility with the resin, and fluidity of a mixture with the resin.

It is preferable that the temperature of the solid particles fed into the pyrolysis tank is +50° C. or higher and +250° C. or lower in the pyrolysis tank. By setting the temperature of the solid particles fed into the pyrolysis tank to be +50° C. or higher in the pyrolysis tank, it is possible to increase the pyrolysis rate of the resin. By setting the temperature of the solid particles fed into the pyrolysis tank to be +250° C. or less in the pyrolysis tank, it is possible to improve the quality of the pyrolysis products recovered by pyrolyzing the resin.

The amount of heat fed to the pyrolysis tank by the solid particles increases as the temperature of the solid particles increases and the feeding rate of the solid particles increases. In order to stably pyrolyze the resin, it is preferable that a ratio of the feeding rate (kg/hr) of the solid particles to the feeding rate (kg/hr) of the resin is in the range of 1 to 20. When the ratio of the feeding rate (kg/hr) of the solid particles to the feeding rate (kg/hr) of the resin is too low, though the feeding rate of the solid particles can be reduced and therefore the equipment cost regarding the feeding of the solid particles can be reduced, the feeding temperature of the solid particles has to be extremely increased and it is thereby disadvantageous from the point of view of operation cost. When the ratio is too high, it is not necessary to extremely increased the feeding temperature of the solid particles, but it is necessary to increase the feeding rate of the solid particles. Therefore, it is disadvantageous from the point of view of equipment cost regarding the feeding of the solid particles.

In the first embodiment, it is preferable that the fluidization gas used to fluidize the solid particles and the resin in the pyrolysis tank is a gas not substantially including oxygen from the point of view of stability of the resin pyrolysis and the yield of the pyrolysis products. Examples of the gas used as the fluidization gas include nitrogen, carbon dioxide, steam, and a gas not liquefied by the cooling unit among the products generated by the decomposition of the resin. As the fluidization gas, one kind of gas or mixture gas of two or more kinds of gas may be used. The oxygen concentration in the fluidization gas is preferably 3% by volume or less and more preferably 1% by volume or less, from the point of view of maintenance of stability of the resin pyrolysis, increases in the amount of the recovered liquid, and in the improvement of the quality of the liquid.

The temperature of the fluidization gas fed into the pyrolysis tank is preferably in the range of 0° C. to 500° C. By setting the temperature of the fluidization gas to be 0° C. or higher, it is possible to prevent the excessive decrease in temperature of the pyrolysis tank. By setting the temperature of the fluidization gas to be 500° C. or lower, it is possible to improve the quality of the liquid recovered by pyrolyzing the resin.

It is preferable that the feeding position of the fluidization gas in the pyrolysis tank is in a lower portion of the pyrolysis tank. The lower portion of the pyrolysis tank means a position between the lowermost end of the pyrolysis tank to the feeding position of the resin. The lowermost end of the pyrolysis tank is a vertex-corresponding position of a cone when the lowermost surface of the pyrolysis tank has a cone shape and is in a position on the lowermost surface of the pyrolysis tank when the lowermost surface of the pyrolysis tank has a plane shape.

By feeding the fluidization gas between the lowermost portion of the pyrolysis tank and the feeding position of the resin, the solid particles or the resin can be smoothly fluidized and thus both can be uniformly dispersed. From the point of view of fluidity in the pyrolysis tank, the fluidization gas is preferably fed into the pyrolysis tank while being dispersed by a gas distributor. Examples of the gas distributor include a porous plate, a slit plate, a mesh plate, a sintered filter, a nozzle, and a nozzle with a cap.

The ratio of the feeding rate (kg/hr) of the fluidization gas to the feeding rate (kg/hr) of the resin is preferably in the range of 0.4 to 3.0. By setting the ratio of the feeding rate (kg/hr) of the fluidization gas to the feeding rate (kg/hr) of the resin to be 0.4 or more, the fluidity in the pyrolysis tank can be maintained. By setting the ratio to be 3.0 or less, the load of the cooling unit can be reduced.

Examples of the resin used in the first embodiment include polyethylene, polypropylene, polyvinyl chloride, polyethylene terephthalate, polycarbonate, polystyrene, and a (meth) acryl resin. They may be used alone or in a combination of two or more kinds. Here, "(meth)acryl" means acryl and methacryl, or acryl or methacryl.

Examples of major components of the pyrolysis products include paraffin or wax from polyethylene or polypropylene, terephthalic acid from polyethylene terephthalate, phenols from polycarbonate, styrene monomers from polystyrene, and (meth)acryl monomers from the (meth)acryl resin.

As the resin used in the first embodiment, the (meth)acryl resin is preferably used from the point of view of the yield of monomers of the pyrolysis products. Accordingly, it is industrially advantageous that the method according to the present invention is applied to a (meth)acryl resin.

Examples of the monomers of the (meth)acryl resin include acrylic acid, methacrylic acid, and esters thereof. Examples of acrylate include methyl acrylate, ethyl acrylate, and butyl acrylate. Examples of methacrylate include methyl methacrylate, ethyl methacrylate, and butyl methacrylate.

The resin may include monomers other than the above-mentioned monomers as a copolymerization component. Examples of these monomers include maleic anhydride, styrene, α-methyl styrene, and acrylonitrile.

The (meth)acryl resin may be a cross-linked resin. The cross-linked (meth)acryl resin includes a multifunctional monomer unit and a monomer unit constituting the (meth) acryl resin. An example of the multifunctional monomer is multifunctional (meth)acrylate. Examples of multifunctional (meth)acrylate include ethylene glycol diacrylate, propylene glycol diacrylate, 1,4-butanediol diacrylate, 1,6-hexanediol diacrylate, neopentyl glycol diacrylate, ethylene glycol dimethacrylate, propylene glycol dimethacrylate, 1,4-butanediol dimethacrylate, 1,6-hexanediol dimethacrylate, and neopentyl glycol dimethacrylate.

From the point of view of recovering monomers at a high yield, (meth)acryl resin preferably includes 50% by mass or more, and more preferably includes 70% by mass or more of methyl methacrylate as a constituent unit with respect to 100% by mass of the total monomers constituting (meth)acryl resin.

The resin used in the first embodiment may be mixed with other polymers. The resin used in the first embodiment may be complex including a filler. Examples of the filler include aluminum hydroxide, silica, calcium carbide, glass fiber, talc, and clay.

The resin used in the first embodiment may include various additives other than the filler. Examples of the additives include pigments, dyes, reinforcing agents, antioxidants, and various stabilizers.

The gaseous pyrolysis products generated by the pyrolysis of the resin are extracted from the pyrolysis tank along with the fluidization gas and are sent to the cooling unit. The extraction position of the mixture of the fluidization gas and the gaseous pyrolysis products in the pyrolysis tank is preferably located in the space portion of the pyrolysis tank. By extracting the mixture from the space portion, the amount of the solid particles included in the mixture gas of the fluidization gas and the gaseous products of the resin can be reduced.

The cooling unit is not particularly limited, and examples thereof include a tubular heat exchanger, a plate heat exchanger, a scrubber, and a spray tower.

Since some liquid formed by liquidation in by the cooling unit may exist as mist in the fluidization gas, it is preferable that a mist recovering unit is provided in the back of the cooling unit.

A recovery container is disposed in the cooling unit or the mist recovering unit and recovers the pyrolysis products generated by the pyrolysis of the resin as a liquid. The mixture gas of the fluidization gas and the pyrolysis products of the resin not liquefied is discharged from the mist recovering unit. The mixture gas may be discharged to the outside of the system after a cleaning process or may be fed into the pyrolysis tank again. When the mixture gas discharged from the mist recovering unit is fed into the pyrolysis tank again, gas fed from another process may be mixed therewith. The kind of the fed gas is preferably nitrogen, carbon dioxide, or steam from the point of view of improvement in yield of the liquid to be recovered and improvement in quality.

It is preferable that the mass ratio of the gas fed from another process to the mixture gas discharged from the mist recovering unit is in the range of 0 to 5. The ratio of 0 means that the gas not liquefied by the cooling unit among the pyrolysis products of the resin is used as the fluidization gas of the pyrolysis tank. By setting the ratio to be 5 or less, the amount of gas fed from another process can be reduced, thereby reducing the cost for using the gas. The mixture gas can be divided into gas sent to the pyrolysis tank and gas discharged from the system after a cleaning process, by a flow rate controller or a control valve.

It is preferable that the temperature of the fluidization gas refed ito the pyrolysis tank is in the range of 0° C. to 500° C. By setting the temperature of the mixture gas to be higher than the temperature of the resin to be fed, it is possible to prevent the excessive decrease in temperature of the pyrolysis tank. By setting the temperature of the mixture gas to be 500° C. or less, it is possible to improve the quality of the liquid recovered by pyrolyzing the resin.

A second embodiment of the present invention will be described below. The same terms or conditions as in the first embodiment may not be described.

Equipment for putting the second embodiment into practice is referred to FIG. 6.

Heated solid particles, fluidization gas, and resin are continuously fed into the pyrolysis tank. By using the fluidization gas, it is possible to efficiently recover pyrolysis products from the resin. As described above, gas substantially not including oxygen and not liquefied by the cooling unit can be used as the fluidization gas. For example, a mixture of nitrogen fed by a nitrogen feeding blower and the like and a gaseous pyrolysis product not liquefied by the cooling unit among the pyrolysis products of the resin can be used. When methacryl resin having a methyl methacrylate unit is used as the resin, carbon dioxide can be used as a gaseous pyrolysis product not liquefied between the boiling point and the melting point of methyl methacrylate. A ratio of the feeding rate of the fluidization gas A (kg/hr) to the feeding rate of the solid particles B (kg/hr) is in the range of 0.04 to 0.3. By setting the ratio to be 0.04 or more, the flow in the pyrolysis tank can be improved. By setting the ratio to be 0.3 or less, the amount of fluidization gas can be reduced and the amount of solid particles included in the mixture gas of the pyrolysis products and the fluidization gas can be reduced.

It is preferable that the ratio of the feeding rate of the fluidization gas A (kg/hr) to the feeding rate of the resin C (kg/hr) is in the range of 0.4 to 3.0. By setting the ratio to be 0.4 or more, it is possible to rapidly send the pyrolysis products to a recovery process including the cooling unit. By setting the ratio to be 3.0 or less, the amount of fluidization gas to be used can be reduced and the amount of solid particles included in the mixture gas of the pyrolysis products and the fluidization gas can be reduced.

In the second embodiment, the solid particles and the resin are fluidized using both the agitator and the fluidization gas. By providing the pyrolysis tank with the agitator, the flows in the horizontal direction and the vertical direction of the solid particles and the resin in the pyrolysis tank can be improved. The number of agitating shafts of the agitator is not limited and may be 1 or 2 or more. In this embodiment, since the solid particles and the resin are fluidized using both the agitator and the fluidization gas, the flow in the pyrolysis tank is good even if one agitating shaft is equipped in the agitator. When the number of agitating shafts is 2 or more, the flows in the horizontal direction and the vertical direction in the pyrolysis tank are further improved.

The shape of the agitating blade of the agitator is not particularly limited and examples thereof include a paddle blade, an anchor blade, a ribbon blade, a helical blade, a propeller blade, and a turbine blade.

The mean residence time of the solid particles in the pyrolysis tank is in the range of 0.5 hr to 1.5 hr. Here, the "mean residence time" of the solid particles is defined as follows.

[Mean residence time (hr)]=[The amount of solid particles retained in pyrolysis tank (kg)]/[The feeding rate of solid particles (kg/hr)]

Usually, since the equipment is operated so as to keep the amount of solid particles retained in the pyrolysis tank constant, the discharging rate (kg/hr) of the solid particles from the pyrolysis tank is equal to the feeding rate (kg/hr) of the solid particles to the pyrolysis tank.

When the mean residence time of the solid particles is less than 0.5 hr, the resin cannot be sufficiently pyrolyzed in the pyrolysis tank and the amount of resin discharged along with the solid particles increases, thereby not enhancing the amount of pyrolysis products to be recovered. When the mean residence time of the solid particles is greater than 1.5 hr, the pyrolysis tank should be enlarged to increase the amount of solid particles retained in the pyrolysis tank, or the feeding rate of the solid particles has to be reduced. When the pyrolysis tank is enlarged, it is disadvantageous in equipment cost. When the feeding rate of the solid particles is reduced, the sufficient amount of heat necessary for pyrolyzing the resin cannot be supplied and thus it is disadvantageous in terms of efficiency for recovering the pyrolysis products.

The kind of solid particles used in the second embodiment is not particularly limited and the particles described in the first embodiment can be used. Among them, sand is desirable and river sand, mountain sand, and sea sand can be used. The river sand having excellent fluidity is particularly desirable.

The size of solid particles used in the second embodiment is not particularly limited, and the average particle size is preferably in the range of 0.01 mm to 1 mm from the point of view of the handling property and more preferably in the range of 0.05 mm to 0.8 mm.

The resin described in the first embodiment can be used as the resin used in the second embodiment, and (meth)acryl resin is desirable. Examples of the monomer units other than methyl methacrylate constituting (meth)acryl resin include the units of acrylic acid, methacrylic acid, and esters thereof. Examples of the acrylate ester can include methyl acrylate, ethyl acrylate, and butyl acrylate. Examples of methacrylate ester can include ethyl methacrylate and butyl methacrylate.

Among (meth)acryl resin, (meth)acryl resin including a methyl methacrylate unit is desirable. From the point of view of recovering monomers at a high yield, (meth)acryl resin preferably includes 50% by mass or more, and more preferably includes 70% by mass or more of methyl methacrylate as a constituent unit with respect to 100% by mass of the total monomers constituting (meth)acryl resin.

The (meth)acryl resin may include monomer units other than the above-mentioned monomer units as copolymerization components. Examples of these monomer units can include maleic anhydride, styrene, α-methyl styrene, and acrylonitrile.

The (meth)acryl resin may be a cross-linked resin. The cross-linked (meth)acryl resin includes a multifunctional monomer unit and a monomer unit constituting the (meth) acryl resin. An example of the multifunctional monomer is multifunctional (meth)acrylate. Examples of multifunctional (meth)acrylate include ethylene glycol diacrylate, propylene glycol diacrylate, 1,4-butanediol diacrylate, 1,6-hexanediol diacrylate, neopentyl glycol diacrylate, ethylene glycol dimethacrylate, propylene glycol dimethacrylate, 1,4-butanediol dimethacrylate, 1,6-hexanediol dimethacrylate, and neopentyl glycol dimethacrylate.

The resin used in the second embodiment may be mixed with other polymers. The resin used in the second embodiment may be a complex including a filler. Examples of the filler include aluminum hydroxide, silica, calcium carbide, glass fiber, talc, and clay.

The resin used in the second embodiment may include various additives other than the filler. Examples of the additives include pigments, dyes, reinforcing agents, antioxidants, and various stabilizers.

The feeding position of the resin in the pyrolysis tank at the time of feeding the resin into the pyrolysis tank is not particularly limited, but it is preferable that the resin is continuously fed into the pyrolysis tank from a position which is ½ or less of the height of the solid particle layer in the pyrolysis tank in a stationary state.

The height of the solid particle layer in a stationary state is not limited, but is preferably set so that the ratio of the height of the solid particle layer in the stationary state to the representative length of the pyrolysis tank is in the range of 0.5 to 3.5. The reason is the same as described in the first embodiment.

A space portion is preferably disposed above the solid particle layer. The length of the space portion in the stationary state is preferably set so that the ratio of the length of the space portion in the stationary state to the representative length of the pyrolysis tank is in the range of 0.5 to 5.0. The reason is the same as described in the first embodiment.

The total height of the pyrolysis tank is preferably set so that the ratio of the total height of the pyrolysis tank to the representative length of the pyrolysis tank is in the range of 1 to 8.5. The reason is the same as described in the first embodiment.

The size of the resin particles is not particularly limited, but the average particle size of the resin pellets is preferably in the range of 1 to 20 mm and more preferably in the range of 3 to 10 mm from the point of view of handling property, feeding stability, and dispersibility in the pyrolysis tank. By setting the average particle size to be 1 mm or more, it is possible to prevent attachment or fusion bonding between the resin pellets. By setting the average particle size to be 20 mm or less, the dispersibility of the resin pellets in the solid particles is improved.

The feeding of the resin into the pyrolysis tank is preferably performed by the use of an apparatus such as a single screw and a twin screw, from the point of view of quantitative supply. The feeding rate of the resin can be measured by the use of a mass measuring instrument such as a load cell attached to a resin hopper. The feeding rate is controlled by controlling the number of rotations of a feeding screw.

The temperature of the resin fed into the pyrolysis tank is preferably 0° C. or more from the point of view of preventing a decrease in temperature of the pyrolysis tank and maintaining the fluidity in the pyrolysis tank. From the point of view of feeding the resin in a solid state and preventing the fusion bonding between the resin to improve the miscibility of the resin with the solid particles, the temperature of the resin is preferably (Tg−50)° C. or less, or (Tm−50)° C. or less. Here, Tg represents the glass transition temperature of the resin and Tm represents the melting point. The temperature of the resin can be controlled by heating or cooling the hopper in which the resin is stored.

The solid particles heated by a heater are fed into the pyrolysis tank. The feeding position of the solid particles fed continuously into the pyrolysis tank is not particularly limited. Since the inside of the pyrolysis tank is fluidized by the fluidization gas and the agitator, the solid particles can be easily fluidized uniformly in the pyrolysis tank even when they are fed from any position.

As a method of feeding the heated solid particles into the pyrolysis tank, a method of feeding the heated solid particles by a free-fall drop of the solid particles or a method of feeding the heated solid particles using an apparatus such as a single screw or a twin screw are. The method by the free-fall drop of the solid particles is advantageously simple and low in equipment cost. The method using a screw is advantageous from the point of view of quantitative feeding. The feeding rate of the solid particles can be measured using a mass measuring instrument such as a load cell attached to a solid particle hopper. The feeding rate can be controlled by controlling the number of rotations of a rotary valve attached to the solid particle hopper or controlling the number of rotations of a feeding screw.

It is preferable that the temperature of the solid particles fed into the pyrolysis tank is in the range of (T+50)° C. to (T+250)° C. Here, T represents the temperature (° C.) inside the pyrolysis tank.

The temperature of the solid particles is controlled by a solid particle temperature controller disposed in a heater to be described later. Specifically, a thermocouple is disposed at a position where the solid particles exist in the heater to be described later and the amount of fuel supplied is controlled so that the temperature is maintained at a predetermined temperature.

Usually, the feeding rate of the solid particles fed into the pyrolysis tank is equal to the discharging rate of the solid particles discharged from the pyrolysis tank so as to keep the amount of solid particles retained in the pyrolysis tank constant.

The discharging position of the solid particles is preferably lower than the height of the feeding position of the resin. The resin is hardly mixed into the solid particles discharged from the lower portion lower than the height of the feeding position of the resin and the fluidity of the solid particles is secured, thereby increasing the amount of pyrolysis products to be recovered. On the contrary, when the solid particles are discharged from the same height as the feeding position of the resin or from above the height, the large amount of the resin is mixed into the solid particles. Accordingly, the fluidity is poor and the dischargeability of the solid particles is poor, thereby reducing the amount of pyrolysis products to be recovered.

The discharging of the solid particles from the pyrolysis tank is preferably performed using an apparatus such as a single screw or a twin screw, from the point of view of quantitative feeding. The discharging rate of the solid particles can be measured using a mass measuring instrument such as a load cell attached to the solid particle hopper. The discharge rate can be controlled by controlling the number of rotations of a solid particle discharging screw.

The feeding position of the fluidization gas in the pyrolysis tank is preferably in the lower portion of the pyrolysis tank from the point of view of fluidization of the resin and the solid particles and the uniform dispersion thereof.

From the point of view of excellent fluidity in the pyrolysis tank, the fluidization gas is preferably fed into the pyrolysis tank while being dispersed by a distributor. Examples of the distributor include a porous plate, a slit plate, a mesh plate, a sintered filter, a nozzle, and a nozzle with a cap.

From the point of view of quantitative feeding, it is preferable that a blower or the like is used to feed the fluidization gas into the pyrolysis tank. The feeding rate of the fluidization gas can be measured and controlled by the use of a gas flow rate controller such as a vortex flowmeter.

The temperature of the fluidization gas can be controlled using a temperature controller disposed upstream than the pyrolysis tank. Specific examples thereof include an electric heater and a heat exchanger.

The temperature of the fluidization gas fed into the pyrolysis tank is preferably 0° C. or more from the point of view of preventing a decrease in temperature of the pyrolysis tank or maintaining the fluidity in the pyrolysis tank. It is preferable from the point of view of efficiently recovering the pyrolysis products that the temperature of the fluidization gas is 500° C. or less.

It is preferable that the extracting position of the mixture gas of the gaseous pyrolysis products and the fluidization gas in the pyrolysis tank is the space portion above the solid particle layer in the pyrolysis tank. By extracting the mixture gas from the space portion, it is possible to prevent the solid particles from being mixed into the mixture gas of the gaseous pyrolysis products and the fluidization gas. The extracted mixture gas of the gaseous pyrolysis products and the fluidization gas is sent to a recovery process.

An apparatus for capturing the solid particles may be provided further upstream than the recovery process. An example thereof is a cyclone.

The recovery process includes cooling and recovering the gaseous pyrolysis products among the pyrolysis products and is equipped with a cooling unit and a container. The cooling unit is not particularly limited, but examples thereof include a tubular heat exchanger, a plate heat exchanger, a scrubber, and a spray tower.

The mixture gas of the pyrolysis products and the fluidization gas is guided to and cooled by the cooling unit in the recovery process. The cooling temperature is between the freezing point (° C.) and the boiling point (° C.) of the pyrolysis product to be recovered. When methyl methacrylate is recovered from (meth)acryl resin, the pyrolysis product (methyl methacrylate) becomes a liquid by cooling the mixture gas to −48° C. to 100° C., but the fluidization gas maintains a gaseous state, whereby both can be separated. Most liquefied pyrolysis products by cooling are collected in a container disposed below the cooling unit. The container serves to collect the liquid pyrolysis products and the size and shape of the container are not limited.

It is preferable that a mist recovering unit is disposed further downstream than the cooling unit. Examples of the mist recovering unit include a cyclone mist recovering unit and a mesh mist recovering unit. A container is disposed below the mist recovering unit and the liquid pyrolysis products are collected in the container. The size and shape of the container are not limited.

The mixture gas of the gaseous or misty pyrolysis products (which are not recovered by the cooling unit) and the fluidization gas is guided to the mist recovering unit and most of the mist is collected in the container disposed below the mist recovering unit. The fluidization gas is discharged from the mist recovering unit and is fed to the pyrolysis tank. The fluidization gas discharged from the mist recovering unit includes the gaseous or misty pyrolysis products not recovered by the mist recovering unit. By feeding the mixture gas into the pyrolysis tank again, it is possible to increase the amount of pyrolysis products recovered.

When the mixture gas discharged from the mist recovering unit is fed to the pyrolysis tank again, nitrogen gas fed from a different process may be mixed therewith. A mass ratio of the nitrogen gas to the mixture gas discharged from the mist recovering unit is preferably in the range of 0.01 to 5. By setting the ratio to be 0.01 or more, it is possible to increase the nitrogen concentration in the pyrolysis tank. By setting the ratio to be 5 or less, the amount of nitrogen gas can be reduced, thereby reducing the cost due to the use of the nitrogen gas. The mixture gas is divided into gas sent to the pyrolysis tank and gas discharged to the outside of the system after the cleaning process, by the use of a flow rate controller or a control valve.

By mixing the nitrogen gas into the mixture gas discharged from the mist recovering unit and discharging some of the mixture gas to the outside of the system by the use of the flow rate controller after the cleaning process, it is possible to reduce the oxygen concentration in the fluidization gas fed into the pyrolysis tank. The oxygen concentration in the fluidization gas fed into the pyrolysis tank is preferably 3% by volume or less and more preferably 1% by volume or less from the point of view of securing the pyrolysis stability of the resin to be recovered, increasing the amount of liquid, and improving the quality of the liquid.

It is preferable that the solid particles discharged from the pyrolysis tank are introduced into a heater to heat the solid particles and fed the heated solid particles into the pyrolysis tank again. The unpyrolyzed resin may be continuously discharged along with the solid particles discharged continuously from the pyrolysis tank.

A fluidized bed or a rotary kiln is used as the heater. The fluidized bed serves to increase the temperature of the solid particles while fluidizing the sand using air, combustion gas of a fuel, or a mixture thereof and to pyrolyze or combust the unpyrolyzed resin. The rotary kiln serves to pyrolyze or combust the unpyrolyzed material by allowing the rotary kiln to rotate while feeding air, combustion gas of a fuel, or a mixture thereof and increasing the temperature of the solid particles while fluidizing the solid particles therein.

It is preferable that, from the point of view of the pyrolysis rate of the resin, particularly, (meth)acryl resin, the temperature T (° C.) in the pyrolysis tank is 350° C. or more. It is preferable that, from the point of view of recovery efficiency of the pyrolysis products, particularly, methyl methacrylate, the temperature of the pyrolysis tank is 500° C. or less.

The temperature in the pyrolysis tank can be measured by a thermocouple disposed in the tank.

The temperature in the pyrolysis tank can be controlled by the feeding rates, temperature, or the like of the fed resin, the heated solid particles, and the fluidization gas. By disposing a jacket, a heater, or a cooling unit inside or outside the pyrolysis tank, the temperature in the pyrolysis tank can be controlled.

EXAMPLES

Hereinafter, examples of the invention will be described, but the invention is not limited to the examples.

The quantities of resin, solid particles, fluidization gas, pyrolysis products, and unpyrolyzed materials are based on mass (kg).

Resin

Methyl methacrylate (hereinafter, referred to as "MMA") was used as the resin (resin of 100 mass %: mass-average molecular weight of 400,000; pellet shape with an average particle size of 5 mm (which passes through a mesh with the opening of 5.6 mm but does not pass through a mesh with the opening of 4.75 mm); glass transition temperature (Tg) of 100° C.).

Solid Particle

Natural river sand (Shouei Material, product name: Ebararozuna, average particle diameter of 0.3 mm, volume density of 1,600 kg/m$^3$) was used as the solid particles.

Measurement of Ratio of Unpyrolyzed Resin in Mixture of Solid Particles and Unpyrolyzed Resin The mixture (mass W1) of the unpyrolyzed materials and the solid particles was left in an air-heating furnace (in air atmosphere) of 800° C. for 1 hour to completely pyrolyze the unpyrolyzed materials. The mass W2 after the complete pyrolysis was measured and the ratio of the unpyrolyzed materials was calculated from the following expression:

[Ratio of unpyrolyzed materials (%)]=(W1−W2)/W1×100

Method of Calculating Ratio of Unpyrolyzed Materials Sent from Pyrolysis Tank to Heating Furnace in Resin to be Fed

[Ratio (%) of unpyrolyzed materials sent from pyrolysis tank to heating furnace in resin to be fed]=[Discharging rate (kg/hr) of mixture of unpyrolyzed materials and solid particles discharged from pyrolysis tank]×[Ratio of unpyrolyzed materials (%)]/[Feeding rate of resin (kg/hr)]

Method of Calculating Ratio of Gaseous Pyrolysis Products Sent from Pyrolysis Tank to Cooling Unit in Resin to be Fed

[Ratio (%) of gaseous pyrolysis products sent from pyrolysis tank to cooling unit in resin to be fed]=100−[Ratio (%) of unpyrolyzed materials sent from pyrolysis tank to heating furnace in resin to be fed]

Evaluation of Pyrolysis Products of Resin (1) Yield of Recovered Liquid (%)

[Yield of recovered liquid (%)]=[Recovering rate of liquid (kg/hr)]/[Feeding rate of resin (kg/hr)]×100

(2) MMA Concentration (% by Mass) in Recovered Liquid

The measurement was performed using a gas chromatography (manufactured by Shimadzu Corporation, GC-17A). N,N-dimethyl formaldehyde was used as a solvent. A calibration curve was prepared in advance and the MMA concentration in the liquid was calculated from the result of a peak ratio of the gas chromatography of the recovered liquid.

Example 1

The equipment shown in FIG. 6 was used. The pyrolysis tank 3 shown in FIG. 1 was used. The pyrolysis tank 3 had a cylindrical upper portion and a conical lower portion and had a diameter of 350 mm. The height from the vertex of the cone to the uppermost surface of the pyrolysis tank 3 was 1400 mm. The agitating blade included two inclined paddle blades arranged in 5 stages. Two paddles had a diameter of 310 mm, a width of 20 mm, an inclination angle of 45°, and a paddle pitch of 140 mm. The upper and lower paddle blades were perpendicular to each other. The agitation speed was 25 revolutions per minute (25 rpm).

A distributor (with a thickness of 1.6 mm and made of stainless) formed of a sintered metal filter (Fuji Filter Manufacturing Co., Ltd.) was disposed in a cone shape in the lower portion of the pyrolysis tank 3 so as to disperse gas. The bottom diameter of the cone was 350 mm and the height of the cone was 100 mm. A pipe for discharging the solid particles was disposed at the center (vertex of the cone) of a conical filter of the distributor.

First, 100 kg of natural river sand was put into the pyrolysis tank 3 and pre-heated at about 420° C. by an electric heater disposed on a side surface of the pyrolysis tank 3. The height of the sand in a stationary state from the vertex of the cone was 720 mm The resin was continuously fed into the pyrolysis tank at 10.0 kg/hr at a position higher by 200 mm from the vertex of the cone. A single screw was used as the resin feeding unit 2. The feeding temperature was set to 20° C. The mixture of the unpyrolyzed materials of the resin and the sand was continuously discharged at 100 kg/hr from the vertex of the cone in the pyrolysis tank 3 by the single screw 2 and was sent to the heating furnace 8. The unpyrolyzed materials were combusted and the temperature of the sand was raised. A fluidized bed for fluidizing the sand using hot air was used in the heating furnace 8. By controlling the temperature of the hot air fed from the lower portion of the fluidized bed, the temperature of the sand right after being discharged from the heating furnace 8 was set to 610° C. The temperature of the sand right before being fed into the pyrolysis tank 3 was 600° C. The feeding rate of the sand from the heating furnace 8 to the pyrolysis tank 3 was set to 100 kg/hr. The feeding position of the heated sand to the pyrolysis tank 3 was higher than the vertex of the cone of the pyrolysis tank 3 by 850 mm and the heated sand was fed by the single screw 6. At the time of starting feeding the resin, the electric heater disposed on the side surface of the pyrolysis tank 3 was stopped.

Mixture gas of gas discharged from the mist recovering unit 11 and nitrogen gas fed from a fluidization gas feeding blower 14 was used as the fluidization gas of the pyrolysis tank 3.

Gas was discharged from the mist recovering unit 11 at about 20 kg/hr. Since the discharged gas includes gas not liquefied among the pyrolysis products of the resin, the amount of discharged gas was slightly more than 20 kg/hr of the fluidization gas fed into the pyrolysis tank 3. The nitrogen gas fed from the gas feeding blower 14 at 2 kg/hr was mixed into the gas discharged from the mist recovering unit 11, and about 2 kg/hr out of about 22 kg/hr was discharged to the outside of the system after the cleaning process and 20 kg/hr was fed to the pyrolysis tank 3, using the flow rate controller 15 (including a vortex flowmeter and a control valve). The oxygen concentration in the gas discharged from the mist recovering unit 11 was 0.0% by volume as a result of measurement using a magnetic oxymeter.

The ratio of the feeding rate (kg/hr) of the fluidization gas and the feeding rate (kg/hr) of the resin was 2.0 (i.e., 20.0/10.0). The feeding temperature of the fluidization gas including nitrogen gas as a major component into the pyrolysis tank 3 was 30° C. The temperature of the pyrolysis tank 3 in a steady state was 400° C.

Some of the mixture of the unpyrolyzed material and the sand discharged from the pyrolysis tank 3 was sampled and the ratio of the unpyrolyzed material was measured to be 0.08%. Accordingly, the unpyrolyzed material was 0.08 kg/hr out of 100.0 kg/hr of the discharged mixture. The ratio of the resin introduced into the heating furnace 8 in the fed resin was 0.8% (i.e., 0.08/10.0×100). From this calculation result, the ratio of the resin introduced into the cooling unit 9 in the fed resin was calculated to be 99.2% (i.e., 100−0.8).

The gaseous pyrolysis products sent to the cooling unit 9 was cooled and recovered as a liquid. The cooling unit 9 is a multitubular condenser and a coolant of −10° C. was made to flow in a jacket thereof. The temperature of the fluid discharged from the multitubular condenser was 3° C. and the fluid was sent to the mist recovering unit 11. The mist recovering unit 11 is of a cyclone type and recovered liquid mist included in nitrogen. A jacket was attached to the mist recovering unit 11 and a coolant of 0° C. was made to flow in the jacket. Recovery containers 10 and 12 for collecting the liquid were disposed below the cooling unit 9 and the mist recovering unit 11, respectively.

As a result of continuous operation for 24 hours after the start of the feeding of the resin, the operation was performed stably. The sum of the liquid collected in the recovery container 10 disposed below the cooling unit 9 and the recovery container 12 disposed below the mist recovering unit 11 was 227.5 kg. In average, the liquid could be recovered at 9.48 kg/hr. The yield of the recovered liquid was calculated to be 94.8% (i.e., 9.48/10.0×100). The MMA concentration in the recovered liquid was 96.2%.

Example 2

The same operation as Example 1 was performed except that the feeding position of the resin was set to be higher by 300 mm from the vertex of the cone. As a result of continuous operation for 24 hours after the start of the feeding of the resin, the operation was performed stably. The yield of the recovered liquid was 94.2%. The MMA concentration in the recovered liquid was 96.6%.

Comparative Example 1

Figure 2:
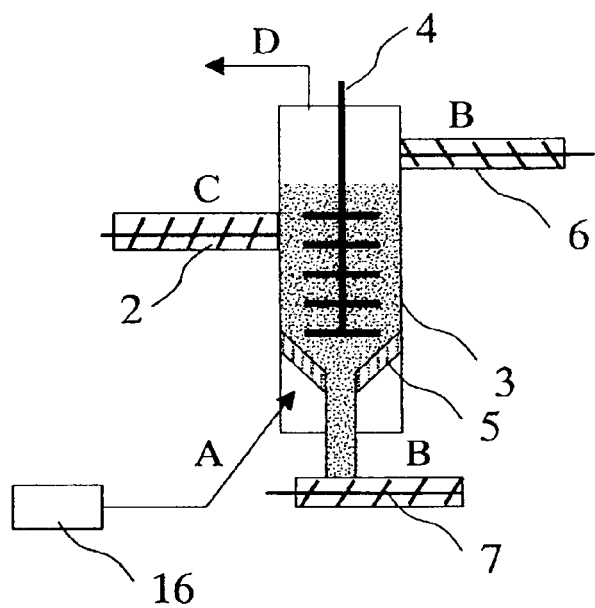
FIG. 2 is a diagram illustrating a pyrolysis tank used in Comparative Example 1.

The same operation as Example 1 was performed except that the pyrolysis tank 3 of FIG. 1 used in Example 1 was replaced with the pyrolysis tank of FIG. 2 and the feeding position of the resin was set to be higher by 400 mm from the vertex of the cone. The operation could be performed for 3 hours after the start of the feeding of the resin, however, thereafter the agitating blade became gradually rotated unstably. The operation was stopped and the inside of the pyrolysis tank 3 was checked. As a result, the sand and the resin were lumped in the upper portion of the pyrolysis tank 3.

Comparative Example 2

Figure 3:
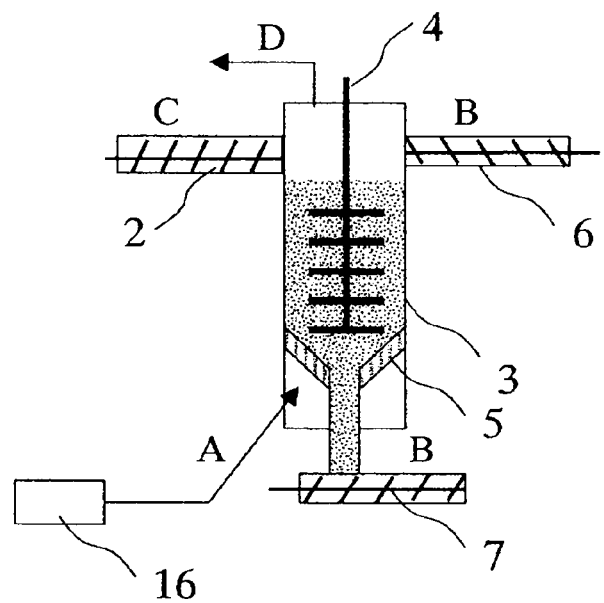
FIG. 3 is a diagram illustrating a pyrolysis tank used in Comparative Example 2.

The same operation as Example 1 was performed except that the pyrolysis tank 3 of FIG. 1 used in Example 1 was replaced with the pyrolysis tank 3 of FIG. 3 and the feeding position of the resin was set to be higher by 850 mm from the vertex of the cone. The operation could be performed for 1 hour after the start of the feeding of the resin, however, thereafter the agitating blade gradually rotated more unstably. The operation was stopped and the inside of the pyrolysis tank 3 was checked. As a result, the sand and the resin were lumped in the upper portion of the pyrolysis tank 3.

Comparative Example 3

Figure 4:
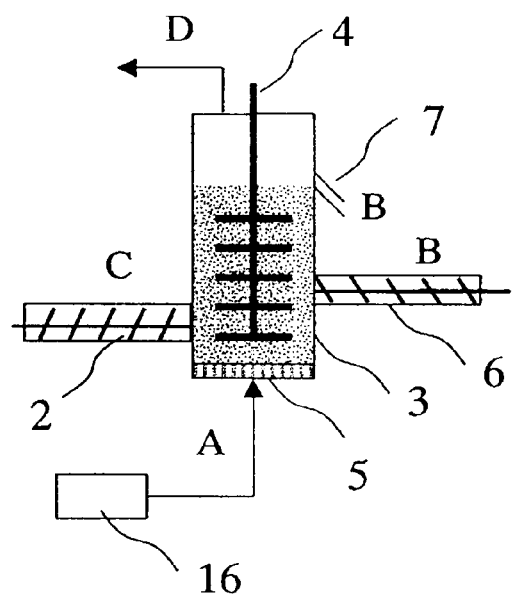
FIG. 4 is a diagram illustrating a pyrolysis tank used in Comparative Example 3.

The same operation as Example 1 was performed except that the pyrolysis tank 3 of FIG. 1 used in Example 1 was replaced with the pyrolysis tank 3 of FIG. 4. A flat-shaped dispersing plate was used as the gas dispersing plate 5 disposed in the lower portion of the pyrolysis tank 3. The height from the dispersing plate 5 to the uppermost surface of the pyrolysis tank 3 was 1400 mm. The pyrolysis tank 3 was filled with the sand of 100 kg and the height of the sand in a stationary state was 650 mm. The resin was fed to a position higher by 200 mm from the dispersing plate 5, the heated sand was fed to a position higher by 300 mm from the dispersing plate 5, and the sand was discharged from the uppermost surface of the sand layer. The screw was not used to discharge the sand from the pyrolysis tank 3, but a free-fall drop method was used.

The sand was not discharged from the pyrolysis tank 3 in 1 hour after the start of the feeding of the resin. As a result of checking a discharge port, a mixture of the sand and the resin clogged the discharge port.

Example 3

Figure 5:
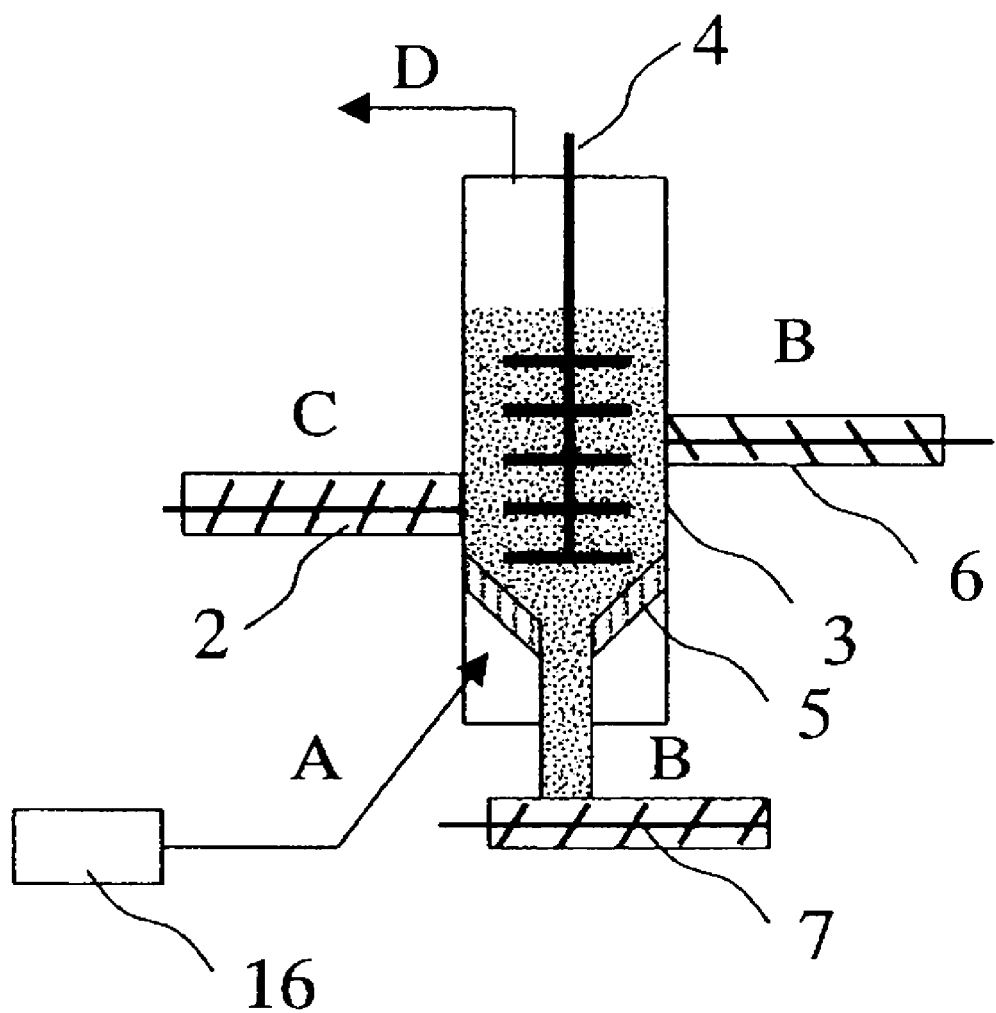
FIG. 5 is a diagram illustrating the second embodiment of a pyrolysis tank used in the present invention.

The same operation as Example 1 was performed except that the pyrolysis tank 3 of FIG. 1 used in Example 1 was replaced with the pyrolysis tank 3 of FIG. 5. The feeding position of the resin was set to be higher by 200 mm from the vertex of the cone and the feeding position of the sand was set to be higher by 400 mm from the vertex of the cone.

The operation could be performed stably for 24 hours after the start of the feeding of the resin. The yield of the liquid was 94.5% and the MMA concentration of the recovered liquid was 96.4%.

The results of Examples 1 to 3 and Comparative Examples 1 to 3 are shown in Table 1.

TABLE 1

|  | Example 1 | Example 2 | Example 3 | Comparative example 1 | Comparative example 2 | Comparative example 3 |
|---|---|---|---|---|---|---|
| Height of sand in stationary state (mm) | 720 | 720 | 720 | 720 | 720 | 650 |
| Feeding position of resin (mm) | 200 | 300 | 200 | 400 | 850 | 200 |
| Feeding position of sand (mm) | 850 | 850 | 400 | 850 | 850 | 300 |
| Discharging position of sand | Vertex of cone | Vertex of cone | Vertex of cone | Vertex of cone | Vertex of cone | Uppermost surface of sand layer |
| Ratio of resin sent from pyrolysis tank to heating furnace (%) | 0.8 | 0.6 | 0.7 | — | — | — |
| Ratio of resin sent from pyrolysis tank to cooling unit (%) | 99.2 | 99.4 | 99.3 | — | — | — |
| Yield of recovered liquid (%) | 94.8 | 94.2 | 94.5 | — | — | — |
| MMA concentration in recovered liquid (%) | 96.2 | 96.6 | 96.4 | — | — | — |

Example 4

Similarly to Example 1, the equipment shown in FIG. 6 was used.

First, 70 kg of natural river sand was put into the pyrolysis tank 3. The height of the sand layer in a stationary state was 520 mm. Thereafter, the inside of the pyrolysis tank 3 was replaced with nitrogen.

The sand was continuously discharged at 120 kg/hr from the pyrolysis tank 3 and was sent to the heating furnace 8. A single screw was used as the discharging unit 7. The discharging rate was measured by the load cell of the solid particle hopper (not shown) disposed between the pyrolysis tank 3 and the single screw 7. The discharging rate was controlled on the basis of the number of rotations of the single screw 7. The fluidized bed for fluidizing the sand using hot air was used as the heating furnace 8 and the sand of 60 kg was put in the heating furnace 8. In the heating furnace 8, the temperature of the sand was made to be a predetermined temperature by controlling the temperature of the hot air.

First, the temperature of the heating furnace 8 was set to 400° C. and the heated sand was continuously fed to the pyrolysis tank 3 at 120 kg/hr. The feeding position was higher by 850 mm from the vertex of the cone of the dispersing plate 5. A single screw was used as the solid particle feeding unit 7. The feeding rate was measured by the load cell of the solid particle hopper (not shown) disposed between the heating furnace 8 and the pyrolysis tank 3. The feeding rate was controlled on the basis of the number of rotations of the single screw 7. The mean residence time of the sand in the pyrolysis tank 3 was calculated to be 0.58 hr (i.e., 70/120).

Nitrogen gas was fed at 20 kg/hr from the dispersing plate 5 and the nitrogen gas from the gas feeding blower 14 at 2 kg/hr was mixed into the nitrogen gas discharged from the mist recovering unit 11. About 2 kg/hr out of the total 22 kg/hr was discharged to the outside of the system and about 20 kg/hr was fed into the pyrolysis tank 3 by the flow rate controller 15 including a vortex flowmeter and a control valve.

By changing the set temperature of the solid particles in the hearing furnace 8 when the temperature of the pyrolysis tank 3 was stabilized at about 400° C., the temperature of the solid particles supplied from the heating furnace 8 to the pyrolysis tank 3 was set to 600° C. and the feeding of the resin to the pyrolysis tank 3 was started. The feeding rate was set to 12 kg/hr and the temperature was set to 20° C. The feeding position was set to be higher by 200 mm from the vertex of the cone of the dispersing plate 5. A single screw was used as the resin feeding unit 2. The feeding rate was measured by the load cell of the resin hopper 1 disposed above the resin feeding screw 2. The feeding rate was controlled on the basis of the number of rotations of the single screw 2.

A ratio of the feeding rate (kg/hr) of the gas including nitrogen gas and the feeding rate (kg/hr) of the resin was 1.67 (i.e., 20/12).

The temperature of the pyrolysis tank 3 became a constant temperature after 30 minutes from the start of the feeding of the resin, where the temperature was 405° C.

On the other hand, the mixture gas of the pyrolysis products of the resin discharged from the pyrolysis tank 3 and the gas including nitrogen gas was sent to a recovery process. The gaseous pyrolysis products sent to the cooling unit 9 was cooled and recovered in a liquid state. The cooling unit 9 was a multitubular condenser and a coolant of −10° C. was made to flow in a jacket thereof. The temperature of the gas discharged from the multitubular condenser 9 was 3° C. and the discharged gas was sent to the mist recovering unit 11. The mist recovering unit 11 was of a cyclone type and recovered the liquid mist included in the gas including the nitrogen gas. A jacket was attached to the mist recovering unit 11 and a coolant of 0° C. was made to flow in the jacket. Recovery containers 10 and 12 for collecting the liquid were disposed below the cooling unit 9 and the mist recovering unit 11, respectively.

The gas including the nitrogen gas was discharged from the mist recovering unit 11 at about 20 kg/hr. Since gas not liquefied among the pyrolysis products of the resin was included in the gas, the amount of discharged gas was slightly greater than 20 kg/hr of the mixture gas fed to the pyrolysis tank 3. The nitrogen gas fed from the gas feeding blower 14 at 2 kg/hr was mixed into the gas discharged from the mist recovering unit 11, and then about 2 kg/hr out of about 22 kg/hr was discharged to the outside of the system after the cleaning process and 20 kg/hr was fed into the pyrolysis tank 3, using the flow rate controller 15 including a vortex flowmeter and a control valve. The temperature of the gas including the nitrogen gas was set to 50° C. by a gas heating unit 16 (heat exchanger using hot air) disposed further downstream than the flow rate controller 15. The ratio of the feeding rate (kg/hr) of the gas including the nitrogen gas into the pyrolysis tank 3 and the feeding rate (kg/hr) of the sand was 0.167 (i.e., 20/120).

As a result of continuous operation for 24 hours after the start of the feeding of the resin, the operation could be performed without any problem. The sum of the liquid collected by the recovery container 10 disposed below the cooling unit 9 and the recovery container 12 disposed below the mist recovering unit 11 was 271.0 kg. In average, the liquid could be recovered at 11.29 kg/hr. The yield of the recovered liquid was calculated to be 94.1% (i.e., 11.29/12.0×100). The MMA concentration in the recovered liquid was 96.5%.

Examples 5 to 7

The same operation as Example 4 was performed except that the amounts of sand retained in the pyrolysis tank 3 were set to 100 kg, 150 kg, and 170 kg. In Examples 6 and 7, the pitch between paddles was set to 200 mm. The heights of the sand layer in a stationary state were 720 mm, 1040 mm, and 1170 mm, respectively.

Comparative Example 4

The same operation as Example 4 was performed except that the amount of sand retained in the pyrolysis tank 3 was set to 55 kg. The height of the sand layer in a stationary state was 420 mm. The operation could be performed for 3 hours after the start of the feeding of the resin, but discharge failure of sand discharged from the pyrolysis tank 3 occurred thereafter. As a result of sampling and observing the sand, the sand and the resin were lumped.

Example 8

The same operation as Example 5 was performed, except that the gas including the nitrogen gas discharged from the mist recovering unit 11 at about 30 kg/hr was mixed with the nitrogen gas fed from the gas feeding blower 14 at 3 kg/hr and then 30 kg/hr out of about 33 kg/hr was fed to the pyrolysis tank 3 by the flow rate controller 15.

Example 9

The same operation as Example 5 was performed, except that the gas including the nitrogen gas discharged from the mist recovering unit 11 at about 15 kg/hr was mixed with the nitrogen gas fed from the gas feeding blower 14 at 1.5 kg/hr and then 15 kg/hr out of about 16.5 kg/hr was fed to the pyrolysis tank 3 by the flow rate controller 15.

Example 10

The same operation as Example 5 was performed, except that the gas including the nitrogen gas discharged from the mist recovering unit 11 at about 10 kg/hr was mixed with the nitrogen gas fed from the gas feeding blower 14 at 1 kg/hr and then 10 kg/hr out of about 11 kg/hr was fed to the pyrolysis tank 3 by the flow rate controller 15.

Example 11

The same operation as Example 5 was performed, except that the gas including the nitrogen gas discharged from the mist recovering unit 11 at about 7 kg/hr was mixed with the nitrogen gas fed from the gas feeding blower 14 at 0.7 kg/hr and then 7 kg/hr out of about 7.7 kg/hr was fed to the pyrolysis tank 3 by the flow rate controller 15, and additionally a ribbon blade was used instead of the paddle blade in the lowermost of the agitation blade and the paddle blade subsequent thereto.

Comparative Example 5

The same operation as Example 11 was performed, except that the gas including the nitrogen gas discharged from the mist recovering unit 11 at about 3 kg/hr was mixed with the nitrogen gas fed from the gas feeding blower 14 at 0.3 kg/hr, and then 3 kg/hr out of about 3.3 kg/hr was fed to the pyrolysis tank 3 by the flow rate controller 15. The operation could be performed for 3 hours after the start of the feeding of the resin, but thereafter the rotation failure of the agitator 4 and the discharge failure of sand discharged from the pyrolysis tank 3 occurred. As a result of observing the inside of the pyrolysis tank 3 after stopping the operation, the sand and the resin were lumped in the vicinity of the agitating blade.

Comparative Example 6

The same operation as Example 5 was performed, except that the gas including the nitrogen gas discharged from the mist recovering unit 11 at about 40 kg/hr was mixed with the nitrogen gas fed from the gas feeding blower 14 at 4 kg/hr, and then 40 kg/hr out of about 44 kg/hr was fed to the pyrolysis tank 3 by the flow rate controller 15. Although the sand was discharged from the pyrolysis tank 3 at 120 kg/hr and was fed to the pyrolysis tank 3 at 120 kg/hr, it was observed that the amount of sand in the pyrolysis tank 3 was gradually reduced. The amount of sand retained in the pyrolysis tank 3 was found out from the pressure drop between the lower portion and the upper portion of the pyrolysis tank 3. As a result of observing the condenser or the mist recovering unit 11 after stopping the operation, the sand was deposited therein.

The results of Examples 4 to 11 and Comparative Example 4 to 6 were shown in Tables 2 and 3.

TABLE 2

|  |  | Example 4 | Example 5 | Example 6 | Example 7 | Comparative example 4 |
|---|---|---|---|---|---|---|
| Feeding rate of resin | kg/hr | 12 | 12 | 12 | 12 | 12 |
| Feeding rate of sand | kg/hr | 120 | 120 | 120 | 120 | 120 |
| Amount of sand retained | kg | 70 | 100 | 150 | 170 | 55 |
| Residence time of sand | hr | 0.58 | 0.83 | 1.25 | 1.42 | 0.46 |
| Feeding rate of fluidization gas including nitrogen gas | kg/hr | 20 | 20 | 20 | 20 | 20 |
| Temperature in pyrolysis tank | °C. | 405 | 402 | 398 | 405 | — |
| Feeding rate of fluidization gas including nitrogen gas/feeding rate of sand | — | 0.167 | 0.167 | 0.167 | 0.167 | 0.167 |
| Feeding rate of fluidization gas including nitrogen gas/feeding rate of resin | — | 1.67 | 1.67 | 1.67 | 1.67 | 1.67 |
| Yield of recovered liquid | % | 94.1 | 95.1 | 95.2 | 94.7 | — |
| MMA concentration | % | 96.5 | 94.7 | 95.8 | 95.1 | — |

TABLE 3

|  |  | Example 8 | Example 9 | Example 10 | Example 11 | Comparative example 5 | Comparative example 6 |
|---|---|---|---|---|---|---|---|
| Feeding rate of resin | kg/hr | 12 | 12 | 12 | 12 | 12 | 12 |
| Feeding rate of sand | kg/hr | 120 | 120 | 120 | 120 | 120 | 120 |
| Amount of sand retained | kg | 100 | 100 | 100 | 100 | 100 | 100 |
| Residence time of sand | hr | 0.83 | 0.83 | 0.83 | 0.83 | 0.83 | 0.83 |
| Feeding rate of fluidization gas including nitrogen gas | kg/hr | 30 | 15 | 10 | 7 | 3 | 40 |
| Temperature in pyrolysis tank | °C. | 399 | 404 | 405 | 407 | — | — |
| Feeding rate of fluidization gas including nitrogen gas/feeding rate of sand | — | 0.250 | 0.125 | 0.083 | 0.058 | 0.025 | 0.333 |
| Feeding rate of fluidization gas including nitrogen gas/feeding rate of resin | — | 2.50 | 1.25 | 0.83 | 0.58 | 0.25 | 3.33 |
| Yield of recovered liquid | % | 94.8 | 95.0 | 95.2 | 94.9 | — | — |
| MMA concentration | % | 95.4 | 95.9 | 96.1 | 95.4 | — | — |

INDUSTRIAL APPLICABILITY

The invention can be widely applied as methods of efficiently recovering methyl methacrylate by pyrolyzing methacryl resin.

The invention claimed is:

1. A method of recovering a pyrolysis product of a resin as a liquid pyrolysis product by cooling a gaseous pyrolysis product generated from pyrolysis of the resin in a pyrolysis tank, the method comprising the following (1) to (4):
   (1) continuously feeding fluidization gas, heated solid particles, and a resin into the pyrolysis tank to fluidize the solid particles and the resin by the fluidization gas;
   (2) continuously feeding the resin into the pyrolysis tank from a position which is ½ or less of the height of a solid particle layer in the pyrolysis tank in a stationary state;
   (3) continuously discharging the solid particles from a position lower than the height of a feeding position of the resin; and
   (4) heating the discharged solid particles in a heating furnace and then feeding the heated solid particles into the pyrolysis tank.

2. The method according to claim 1, wherein the solid particles and the resin in the pyrolysis tank are agitated by an agitator.

3. The method according to claim 1, wherein a ratio A/C of a feeding rate of the fluidization gas A (kg/hr) to a feeding rate of the resin C (kg/hr) is in the range of 0.4 to 3.0.

4. The method according to claim 1, wherein the temperature of the solid particles fed into the pyrolysis tank is in the range of (T+50)° C. to (T+250)° C., the temperature of the fluidization gas fed into the pyrolysis tank is in the range of 0° C. to 500° C., and the temperature of the resin fed into the pyrolysis tank is in the range of 0° C. to (Tg−50)° C. or the range of 0° C. to (Tm−50)° C., where T represents the temperature of the pyrolysis tank, Tg represents the glass transition temperature of the resin, and Tm represents the melting point of the resin.

5. The method according to claim 1, wherein the fluidization gas comprises nitrogen gas.

6. The method according to claim 1, wherein the solid particles are sand.

7. The method according to claim 1, wherein the resin is a (meth)acryl resin and the pyrolysis product to be recovered is methyl methacrylate.

8. A method of recovering a pyrolysis product of a resin as a liquid pyrolysis product by cooling a gaseous pyrolysis product generated from pyrolysis of the resin in a pyrolysis tank, the method comprising the following (1) to (7):
   (1) continuously feeding heated solid particles, fluidization gas, and a resin into the pyrolysis tank, provided that the fluidization gas is fed from the lower portion of the pyrolysis tank;
   (2) setting the temperature T of the pyrolysis tank to the range of 350° C. to 500° C.;
   (3) fluidizing the solid particles and the resin with an agitator disposed in the pyrolysis tank and the fluidization gas;
   (4) setting a ratio A/B of a feeding rate of the fluidization gas A (kg/hr) to a feeding rate of the solid particles B (kg/hr) to the range of 0.04 to 0.3;
   (5) continuously discharging the solid particles from the pyrolysis tank while the mean residence time of the solid particles in the pyrolysis tank is maintained to the range of 0.5 to 1.5 hr;
   (6) discharging mixture gas of the gaseous pyrolysis product generated from the resin pyrolyzed by sensible heat of the solid particles and the fluidization gas from the pyrolysis tank and cooling the mixture gas in a cooling unit to liquefy the pyrolysis product; and
   (7) separating the fluidization gas from the cooled mixture gas and feeding the separated fluidization gas into the pyrolysis tank again.

9. The method according to claim 8, wherein a ratio A/C of a feeding rate of the fluidization gas A (kg/hr) to a feeding rate of the resin C (kg/hr) is in the range of 0.4 to 3.0.

10. The method according to claim 8, wherein the solid particles discharged from the pyrolysis tank are introduced into a heating furnace and the heated solid particles are fed into the pyrolysis tank again.

11. The method according to claim 8, wherein the temperature of the solid particles fed into the pyrolysis tank is in the range of (T+50)° C. to (T+250)° C., the temperature of the fluidization gas fed into the pyrolysis tank is in the range of 0° C. to 500° C., and the temperature of the resin fed into the pyrolysis tank is in the range of 0° C. to (Tg−50)° C. or the range of 0° C. to (Tm−50)° C., where T represents the temperature of the pyrolysis tank, Tg represents the glass transition temperature of the resin, and Tm represents the melting point of the resin.

12. The method according to claim 8, wherein the fluidization gas comprises nitrogen gas.

13. The method according to claim 8, wherein the solid particles are sand.

14. The method according to claim 8, wherein the resin is (meth)acryl resin and the pyrolysis product to be recovered is methyl methacrylate.

15. The method according to claim 1, wherein the resin is fed in a pellet shape and having an average particle size of 1 to 20 mm.

16. The method according to claim 15, wherein the average particle size of 3 to 10 mm.

17. The method according to claim 8, wherein the resin is fed in a pellet shape and having an average particle size of 1 to 20 mm.

18. The method according to claim 17, wherein the average particle size of 3 to 10 mm.

19. The method according to claim 1, wherein the solid particles have an average particle size of 0.01 mm to 1 mm.

20. The method according to claim 8, wherein the solid particles have an average particle size of 0.01 mm to 1 mm.

* * * * *